United States Patent
Baschong et al.

(10) Patent No.: US 6,514,950 B1
(45) Date of Patent: Feb. 4, 2003

(54) USE OF POLYANIONIC AND POLYANIONICALLY-DERIVATISED NATURAL POLYSACCHARIDES FOR INHIBITING ALKALINE PHOSPHATASE

(75) Inventors: Werner Baschong, Basel (CH); Dietmar Hüglin, Eimeldingen (DE); Peter Fankhauser, Ettingen (CH); Gerd Heinemann, Schliengen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/581,876
(22) PCT Filed: Dec. 9, 1998
(86) PCT No.: PCT/EP98/07999
§ 371 (c)(1),
(2), (4) Date: Jun. 19, 2000
(87) PCT Pub. No.: WO99/32073
PCT Pub. Date: Jul. 1, 1999

(30) Foreign Application Priority Data

Dec. 22, 1997 (EP) ............................................. 97811012
Jul. 2, 1998 (EP) ............................................. 98810616

(51) Int. Cl.⁷ ......................... A01N 43/04; A61K 7/16; A61K 7/28; A61K 7/18
(52) U.S. Cl. ............................. 514/55; 424/49; 424/50; 424/52
(58) Field of Search ............................. 424/49, 50, 52; 514/55

(56) References Cited

U.S. PATENT DOCUMENTS

| | | | |
|---|---|---|---|
| 4,512,968 A | 4/1985 | Komiyama et al. | 424/48 |
| 4,515,722 A | 5/1985 | Yang et al. | 260/403 |
| 4,627,977 A | 12/1986 | Gaffar et al. | 424/52 |
| 5,094,844 A | 3/1992 | Gaffar et al. | 424/52 |
| 5,777,091 A | 7/1998 | Kuhn et al. | 536/20 |

FOREIGN PATENT DOCUMENTS

| | | |
|---|---|---|
| DE | 3343200 | 5/1984 |
| EP | 0512599 | 11/1992 |
| EP | 0803243 | 10/1997 |
| GB | 2235133 | 2/1991 |
| WO | 95/22310 | 8/1995 |
| WO | 95/30403 | 11/1995 |
| WO | 97/48372 | 12/1997 |

OTHER PUBLICATIONS

Chem. Abstr. 122:282249 for JP 0776523 (1995).

*Primary Examiner*—Jezia Riley
(74) *Attorney, Agent, or Firm*—Kevin T. Mansfield

(57) ABSTRACT

A description is given of the use of polyanionic and polyanionically-derivatised natural polysaccharides or non-derivatised natural polysaccharides for inhibiting alkaline phosphatase and of oral compositions for preventing bacterial plaque, which comprises (a) 0 to 10% by weight of at least one linear molecularly dehydrated polyphosphate salt, and (b) 0.0001 to 5% by weight of a polyanionic or polyanionically-derivatised natural polysaccharide.

12 Claims, No Drawings

USE OF POLYANIONIC AND POLYANIONICALLY-DERIVATISED NATURAL POLYSACCHARIDES FOR INHIBITING ALKALINE PHOSPHATASE

The present invention relates to the use of polyanionic and polyanionically-derivatised natural polysaccharides or non-derivatised natural polysaccharides for inhibiting alkaline phosphatase as well as to oral preparations comprising these compounds.

In the dental area there is often the problem of formation of plaque (tartar, calculus) produced by bacterial adhesion to natural or artificial teeth or to the gum and promoting the development of caries and gum diseases such as periodontosis. Tartar is understood to mean deposits which form at the margin of the gum on the surface of the teeth. These deposits consist both of inorganic material—in particular calcium hydrogenoxylapatite (HAP)—and of organic components, such as epithelial cells, food particles, saliva sediments and different kinds of microorganisms.

This whitish, yellowish or often blotchy tartar is undesirable not only because of its appearance but mainly because it gives constant occasion to irritations of the oral mucosa and to the development of gingivitis and diseases of the teeth and teeth socket. Such deposits are prevented on the one hand by daily dental care and by the concomitant microdecalcification. In addition, it is usually necessary to have the dentist remove tartar mechanically from time to time.

Safe and effective agents for inhibiting tartar formation are, for example, the water-soluble, molecularly dehydrated polyphosphates known as sequestrants and chelating agents, such as hexametaphosphates, tripolyphosphates and pyrophosphates, which prevent the formation of HAP (cf. U.S. Pat. No. 4,515,722). In oral application, however, the effect of these compounds is significantly reduced by the saliva enzymes present in the mouth and throat area, such phosphate compounds being hydrolysed in particular by alkaline phosphatases.

U.S. Pat. No. 5,094,844 proposes to reduce the deactivating effect of alkaline phosphatase, i.e. the hydrolysis of the linear molecularly dehydrated polyphosphates, by addition of an anionic polyvinyl phosphonate.

It is the object of this invention to provide further agents which reduce the negative effect of alkaline phosphatase.

Surprisingly, it has now been found that the use of polyanionic and polyanionically-derivatised natural polysaccharides or non-derivatised natural polysaccharides has an inhibiting effect on alkaline phosphatase.

Accordingly, this invention relates to the use of polyanionic and polyanionically-derivatised natural polysaccharides or non-derivatised natural polysaccharides for inhibiting alkaline phosphatase.

In particular, this invention relates to the use of polyanionic and polyanionically-derivatised natural polysaccharides for inhibiting alkaline phosphatase.

The polyanionic and polyanionically-derivatised natural polysaccharides used are preferably
  mucopolysaccharides and other polyanionic natural polysaccharides, such as hyaluronic acid or carageenan,
  polyanionic derivatives, for example sulfates, methylcarboxylates, phosphates etc. of natural, nonanionic polysaccharides, such as dextrans, xanthans, glucans.

Polyanionically-derivatised natural polysaccharides are preferably those compounds which contain phosphate groups, phosphonate groups or methylphosphonate groups, such as chitin derivatives, for example sulfochitins, carboxymethylchitins, phosphochitins or, in particular, chitosan derivatives, for example sulfochitosans, carboxymethylchitosans or, very particularly, phosphochitosans.

The polyanionic and polyanionically-derivatised natural polysaccharides used according to this invention preferably have a molecular weight of >5000.

Preferred phosphochitosans are in particular phosphonomethylated chitosans corresponding to formula

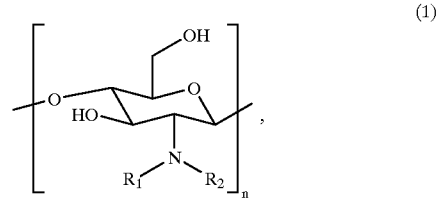

(1)

wherein $R_1$ is hydrogen or a radical of formula

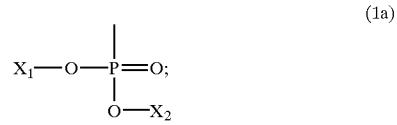

(1a)

$R_2$ is a radical of formula (1a);

$X_1$ and $X_2$ are each independently of the other hydrogen, $C_1$–$C_5$alkyl or an alkali ion or ammonium ion; and n is 20 to 4000.

Very particularly preferred are phosphonomethylated chitosans of formula

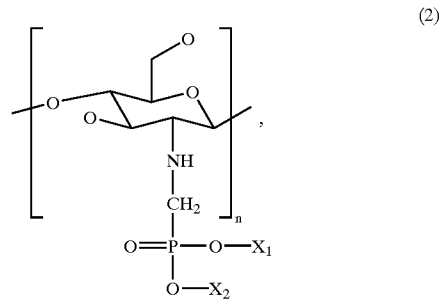

(2)

wherein $X_1$ and $X_2$ are as defined for formula (1).

Most interesting are those compounds of formula (1) or (2), wherein $X_1$ and $X_2$ are each independently of the other alkali metal, and n is 20 to 1000.

The non-derivatised natural polysaccharides used according to this invention are preferably glucans. It is preferred to use β-1,3-glucans corresponding to formula

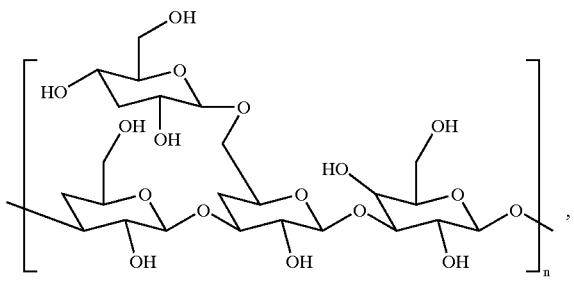

(3)

wherein n is a number corresponding to an average molecular weight (MW) in the range from $>5 \times 10^3$ to $10 \times 10^{10}$ and, very particularly, from $10^5$ to $10^8$.

It has also been found that the polyanionic and polyanionically-derivatised natural polysaccharides and the non-derivatised natural polysaccharides used according to this invention, in particular the phosphonomethylated chitosans of formulae (1) and (2) and the β-glucans of formula (3), inhibit the adhesion of microorganisms, in particular of anaerobic microorganisms, on solid surfaces, especially in holes, interspaces, deposits, pockets in the mouth and throat area, and that they thus reduce or inhibit the negative effects of these germs, in particular the formation of plaque and calculus, or dental decay, bad breath (malodor) and deposits on dentures.

These compounds can also detach the microorganisms from solid surfaces (desorption).

Forming complexes with the Zn, Sn and Mn, Al, Sb, Zr, La, Hf, Ta, Ir, Gd metals, these compounds are furthermore able to desensitise e.g. over-sensitivity on teeth.

The buffer capacity of the phosphonomethylated chitosan stabilises the intrabuccal pH and prevents hyperacidity and hence tooth decay.

In contrast to polyvinyl phosphonates and similar derivatives of synthetic polymers, the phosphonomethylated chitosans of formulae (1) and (2) and the glucans of formula (3) are compounds which are biocompatible and completely bio-degradable.

The preparation of these compounds is carried out by phosphonomethylation of chitosan in a manner known per se. Further details on their preparation may be found in EP-A-0,713,882.

In another of its aspects, this invention relates to an oral composition, which comprises
  (a) 0.01 to 10% by weight, preferably 2 to 5% by weight, of at least one linear molecularly dehydrated polyphosphate salt, and
  (b) 0.0001 to 5% by weight of a polyanionic and polyanionically-derivatised natural polysaccharide.

The polyphosphate salts (=component (a)) used according to this invention, for example the hexametaphosphate, tripolyphosphate and pyrophosphate salts which are effective as active substance against the formation of bacterial plaque in the novel oral composition, are water-soluble alkali metal salts, such as the sodium, potassium or ammonium salts, and mixtures thereof. These compounds are known as agents preventing bacterial plaque from U.S. Pat. Nos. 4,627,977 and 4,806,340.

Component (a) in the novel oral composition is preferably hexametaphosphate, tripolyphosphate, pyrophosphate or mixtures of these compounds.

The polyphosphates can comprise, for example, 2 to 120 phosphorus atoms and are used in the novel oral composition in amounts from 0.01 to 10% by weight, preferably from 2 to 5% by weight, based on the total weight of the composition.

Pyrophosphate is preferably used as a mixture of tetrapotassium pyrophosphate and tetrasodium pyrophosphate.

The novel composition may also contain antimicrobial active substances, for example phenol derivatives, diphenyl compounds, benzyl alcohols, chlorohexidine, $C_{12}$–$C_{14}$alkylbetaine, $C_8$–$C_{18}$fatty acid amidoalkylbetaine, amphoteric surfactants, trihalocarbanilides, quaternary ammonium salts and, very particularly, 2-hydroxydiphenyl ethers of formula

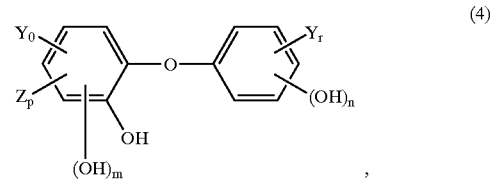

(4)

wherein
  Y is chloro or bromo,
  Z is $SO_2H$, $NO_2$ or $C_1$–$C_4$alkyl,
  r is 0 to 3,
  o is 0 to 3,
  p is 0 or 1,
  m is 0 or 1, and
  n is 0 or 1.

Very particularly preferred compounds are those of formula

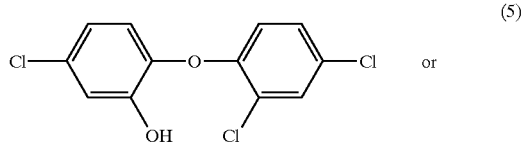

(5)

or

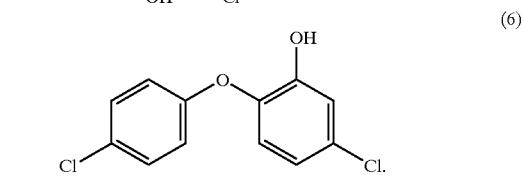

(6)

The novel oral composition can also comprise compounds releasing fluoride ions which are effective against caries formation, for example inorganic fluoride salts, such as sodium fluoride, potassium fluoride, ammonium fluoride or calcium fluoride, or organic fluoride salts, for example amine fluorides which are known under the tradename Olafluor. These compounds may be present in the novel composition in amounts of 0.005 to 3% by weight, depending on solubility and kind of composition.

The novel oral composition is preferably liquid, for example in the form of a mouth wash or mouth rinse, the composition preferably being a 1:1 to 20:1, preferably a 2:1 to 10:1, mixture of water and alcohol.

The pH of the novel oral composition is 4.5 to 9, preferably 5.5 to 8.

The novel oral composition can also be in solid or pasty form, for example in the form of tooth powder, tooth tablet, toothpaste, tooth gel or tooth cream. Such a solid or pasty composition usually comprises an orally acceptable, water-insoluble polishing material. Examples of such polishing materials are water-insoluble metaphosphates, tricalcium phosphates, dehydrated dicalcium phosphates, calcium pyrophosphates, aluminium silicates, zirconium silicates, bentonite, or mixtures of these compounds. The polishing material is usually present in the solid or pasty composition in amounts of 10 to 90% by weight, preferably of 10 to 75% by weight.

The novel oral composition can also contain further materials, for example whitening agents, preservatives, silicones, chlorophyll compounds, other agents for the prevention of bacterial plaque, urea, diammonium phosphates, and mixtures thereof. These adjuvants are present in the novel compositions in such concentrations that the positive properties of the composition are not affected.

Additionally, the novel composition may contain flavouring and sweetening agents, for example peppermint oil, eucalyptus, marjoram, cinnamon, saccharin and the like.

The novel oral composition can be incorporated into lozenges, chewing gum or other products, for example by being stirred into a warm gum material or by coating the exterior surfaces of a chewing gum.

The invention is illustrated by the following Examples.

EXAMPLE 1
Measurement of the Activity of Alkaline Phosphatase

The activity of alkaline phosphatase is measured using the kinetic colour test for clinical-chemical analytical systems (Olympus System Reagents 800, MIT Serice Inc.; San Diego Calif.). Instead of the blood usually used, the source of alkaline phosphatase is a solution comprising 200 µl of a suspension of alkaline phosphatase of *E. coli* (Fluka, CH-9471 Buchs), taken up in 20 ml of 0.1 mol/l tris-HCI buffer, pH 8.0, and prepared with an activity of alkaline phosphatase corresponding to 3 U/ml (U=units), (henceforth called solution (A)).

As measuring solutions, 100 mg of phosphonomethylated chitosan (=P-chitosan) are dissolved in 20 ml of 0.1 mol/l tris-HCI (pH 8.0) and diluted further with 0.1 mol/l each of tris-HCI to 2.5; 0.5; 0.1; 0.05; 0.025; 0.01; 0.0075; 0.005 and 0.0025 mg/ml (solutions B and C).

In order to measure the influence of phosphonomethylated chitosan on the activity of the alkaline phosphatase, 100 µl each of the enzyme solution A are mixed with 900 µl of the dilutions of B or C. According to the clinical-chemical protocol, the activity of the enzyme is determined spectrophotometrically via its ability of degrading the slightly coloured p-nitro-phenylphosphate to the intensely coloured p-nitrophenol (see Table 1).

TABLE 1

| Defined inhibitory concentration [mg/l] | Alk. phosphatase activity [units] phosphonomethylated chitosan | Reference [units] |
|---|---|---|
| 4536 | 205 | |
| 907.2 | 104 | |
| 453.6 | 39 | |
| 90.72 | 15.5 | |
| 45.36 | 23 | |
| 9.072 | 41.5 | |
| 4.536 | 73.5 | |
| 0.9072 | 302 | |
| 0.4536 | 302.5 | |
| 0.09072 | 381.5 | |
| blind | 1 | |
| reference | — | 325.5 |

These results show that phosphonomethylated chitosan effectively reduces the activity of alkaline phosphatase.

EXAMPLE 2
Preparation of a Toothpaste

| Ingredients | % by weight |
|---|---|
| Distilled water | ad 100 |
| D-glucitol | 40.0 |
| Zeodent 113 | 20.0 |
| glycerol | 20.0 |
| tetrasodium pyrophosphate | 12.0 |
| disodium pyrophosphate | 3.40 |
| sodium lauryl sulfate | 1.37 |
| aromatics | 1.35 |
| PEG-6 | 1.33 |
| sodium carboxymethylcellulose | 1.00 |
| sodium fluoride | 0.50 |
| acrylic acid homopolymer | 0.20 |
| saccharin sodium | 0.20 |
| titanium dioxide | 0.16 |
| P-chitosan | 0.03 |
| FD&C Blau Cl 42090 (No. 1, 1% sol.) | 0.03 |

This toothpaste is very effective against bacterial plaque.

EXAMPLE 3
Preparation of a Mouth Wash

| Ingredients | Percent by weight |
|---|---|
| Distilled water | ad 100 |
| ethanol | 10.00 |
| glycerol | 10.00 |
| PEO-PPO-PEO block polymer | 2.00 |
| tetrasodium pyrophosphate | 1.50 |
| aromatics | 1.35 |
| disodium pyrophosphate | 0.50 |
| sodium fluoride | 0.50 |
| saccharin sodium | 0.3 |
| P-chitosan | 0.02 |

This mouth wash is excellently suitable for prophylaxis against bacterial plaque.

EXAMPLE 4
Measurement of the Adsorption and Desorption of Microorganisms a. Adsorption Bacteria: *S. mutans* (ZIB6008); *S. mitis* (KL-stab.); *S. anguinosus* (ZIB6006) and *S. sanguis* (ZIB6010) are plated out anaerobically on BA plates and incubated. One colony each is allowed to grow to a density of about 0.5 $OD_{660}$ in Todd-Hewitt broth as stock solution.

50 mg of hydroxylapatite pearls (HA: Macro-Prep Ceramic Hydroxylapatite, 80 micron, of BioRad) are washed once with 1 ml of sterile $H_2O$ and three times with 1 ml of absorption buffer sterilised by filtration (5 mM KCL, 1 mM $CCl_2$; 0.1 mM $MgCl_2$; 1 mM $K_2HPO_4$, pH 7.2) (cf. Berry & Siragusa (1997); Appl. Environ. Microbiol. 63, 4069–4074). 2 ml of the bacterial solution are centrifuged (10,000 rpm, 5 min) and washed twice with adsorption buffer and are then resuspended in 1 ml of adsorption buffer containing different concentrations of test substance or no test substance. This solution is combined with the hydroxylapatite pearls suspended in 1 ml of adsorption buffer and incubated, with slight shaking, for 30 min at 370° C. After the HA pearls have sedimented, the supernatant is removed. The HA pearls are dissolved in 1.6 ml of 0.5 N HCI. The optical density ($OD_{660}$) of this solution is determined and is placed in relation to the control containing no test substance prepared for each dilution series (control: 100% adsorption).

b. Desorption

Bacteria: S. mutans (ZIB6008); S. mitis (KL-stab.); S. anguinosus (ZIB6006) and S. sanguis (ZIB6010) are plated out anaerobically on BA plates and incubated. One colony each is allowed to grow to a density of about 0.5 $OD_{660}$ in Todd-Hewitt broth as stock solution. 50 mg of hydroxylapatite pearls (HA: Macro-Prep Ceramic Hydroxylapatite, 80 micron, of BioRad) are washed once with 1 ml of sterile $H_2O$ and three times with 1 ml of absorption buffer sterilised by filtration (5 mM KCl, 1 mM $CCl_2$; 0.1 mM $MgCl_2$; 1 mM $K_2HPO_4$, pH 7.2) (cf. Berry & Siragusa (1997); Appl. Environ. Microbiol. 63 4069–4074). 2 ml of the bacterial solution are centrifuged (10,000 rpm, 5 min) and washed twice with adsorption buffer and are then resuspended in 1 ml of adsorption buffer. This solution is combined with the hydroxylapatite pearls suspended in 1 ml of adsorption buffer and incubated, with slight shaking, for 30 min at 37° C. After the HA pearls have sedimented, the supernatant is removed. The HA pearls are washed once with adsorption buffer and are then incubated, with slight shaking, for 30 min at 37° C. with 1 ml of adsorption buffer containing different concentrations of the test substance. After the HA pearls have sedimented, the supernatant is removed and the HA pearls are dissolved in 1.6 ml of 0.5 N HCl. The optical density ($OD_{660}$) of this solution is determined and is placed in relation to the control containing no test substance prepared for each dilution series (control: 0% desorption).

Results:
a. Phosphonomethylated Chitosan
In vitro Inhibition of the Adhesion of Microorganisms Essential for Plaque and Tartar Formation

| Microorganism | P-chitosan [%] | Inhibition +/- [%] | Average error |
|---|---|---|---|
| S. mutans | 0.2 | 76.0 | +/- 5.26 |
| | 0.02 | 38.8 | +/- 7.16 |
| | 0.002 | 27.0 | +/- 4.29 |
| | 0.0002 | 13.4 | +/- 4.14 |
| S. mitis | 0.2 | 84.1 | +/- 0.97 |
| | 0.02 | 67.8 | +/- 3.37 |
| | 0.002 | 27.4 | +/- 6.43 |
| | 0.0002 | 7.1 | +/- 4.56 |
| S. sanguis | 0.200 | 85.1 | +/- 0.81 |
| | 0.02 | 72.7 | +/- 4.84 |
| | 0.002 | 43.6 | +/- 9.05 |
| | 0.0002 | 35.4 | +/- 10.37 |
| S. anguinosus | 0.200% | 74.3% | +/- 3.78 |
| | 0.02% | 43.1% | +/- 10.92 |
| | 0.002% | 24.8% | +/- 9.67 |
| | 0.0002% | 8.5% | +/- 1.44 |

In vitro Desorption of Adhering Microorganisms Essential for Plaque and Tartar Formation

| Microorganism | P-chitosan [%] | Inhibition +/- [%] | Average error |
|---|---|---|---|
| S. mutans | 0.2 | 87.3 | +/- 10.65 |
| | 0.02 | 60.2 | +/- 2.93 |
| | 0.002 | 35.9 | +/- 5.98 |
| | 0.0002 | 14.7 | +/- 8.31 |
| S. mitis | 0.2 | 89.2 | +/- 2.06 |
| | 0.02 | 59.4 | +/- 7.70 |
| | 0.002 | 30.8 | +/- 8.21 |
| | 0.0002 | 17.3 | +/- 7.56 | b. 1.6-1,3-β-Glucan
In vitro Inhibition of the Adhesion of Microorganisms Essential for Plaque and Tartar Formation

| Microorganism | 1-6 1,3-β-Glucan [%] | Inhibition +/- [%] | Average error |
|---|---|---|---|
| S. mutans | 0.2 | 79.8 | +/- 1.68 |
| | 0.02 | 59.3 | +/- 1.53 |
| | 0.002 | 41.0 | +/- 2.53 |
| | 0.0002 | 27.35 | +/- 7.20 |
| S. mitis | 0.2 | 73.1 | +/- 2.72 |
| | 0.02 | 46.7 | +/- 3.67 |
| | 0.002 | 25.6 | +/- 3.09 |
| | 0.0002 | 15.6 | +/- 4.77 |

In vitro Desorption of Adhering Microorganisms Essential for Plaque and Tartar Formation

| Microorganism | 1-6 1,3-β-Glucan [%] | % Desorption | Average error |
|---|---|---|---|
| S. mutans | 0.2 | 79.8 | 1.68 |
| | 0.02 | 59.3 | 1.53 |
| | 0.002 | 41.0 | 2.53 |
| | 0.0002 | 27.35 | 7.20 |
| S. mitis | 0.2 | 73.1 | 2.72 |
| | 0.02 | 46.7 | 3.67 |
| | 0.002 | 25.6 | 3.09 |
| | 0.0002 | 15.6 | 4.77 | c. N-Dicarboxymethylchitosan
In vitro Inhibition of the Adhesion of Microorganisms Essential for Plaque and Tartar Formation

| Microorganism | N-dicarboxymethyl-chitosan [%] | Inhibition +/- [%] | Average error |
|---|---|---|---|
| S. mutans | 0.2 | 48.9 | +/- 8.87 |
| | 0.02 | 19.1 | +/- 9.82 |
| | 0.002 | 14.6 | +/- 4.60 |
| | 0.0002 | 7.5 | +/- 4.60 |
| S. mitis | 0.200 | 42.1 | +/- 5.26 |
| | 0.02 | 32.8 | +/- 3.38 |
| | 0.002 | 23.43 | +/- 2.30 |
| | 0.0002 | 14.5 | +/- 8.05 |

What is claimed is:

1. A method for inhibiting alkaline phosphatase, which comprises treating alkaline phosphatase with an amount of polyanionic or polyanionically-derivatised natural polysaccharides or non-derivatised natural polysaccharides which is effective for inhibiting alkaline phosphatase.

2. A method according to claim 1 wherein polyanionic or polyanionically-derivatised natural polysaccharides for inhibiting alkaline phosphatase are used.

3. A method according to claim 1, wherein the natural polyanionic polysaccharides are mucopolysaccharides and other polyanionic polysaccharides.

4. A method according to claim 1, wherein the polyanionic or polyanionically-derivatised natural polysaccharides have a molecular weight of >5000.

5. A method according to claim 1, wherein the polyanionically-derivatised natural polysaccharides are derived from dextrans, xanthans and glucans.

6. A method according to claim 1, wherein the derivatised natural polysaccharides contain phosphate groups, phosphonate groups or methylphosphonate groups.

7. A method according to claim 1, wherein the natural polysaccharide is chitin.

8. A method according to claim 1, wherein the natural polysaccharide is chitosan.

9. A method according to claim 1, wherein the polyanionically-derivatised polysaccharide is a phosphonomethylated chitosan containing repeating units of the formula

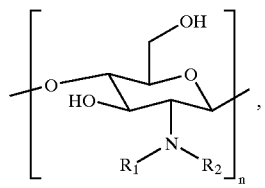

(1)

wherein
R$_1$ is hydrogen or a radical of formula

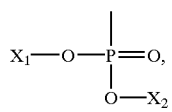

(1a)

R$_2$ is a radical of formula (1a),
X$_1$ and X$_2$ are each independently of the other hydrogen, C$_1$–C$_5$alkyl or an alkali metal ion or ammonium ion, and
n is 20 to 4000.

10. A method according to claim 9, wherein
X$_1$ and X$_2$ are each independently of the other alkali metal, and
n is 20 to 1000.

11. A method according to claim 1, wherein the non-derivatised natural polysaccharide is 1,3-β-glucan.

12. A method according to claim 9, wherein a phosphonomethylated chitosan containing repeating units of the formula

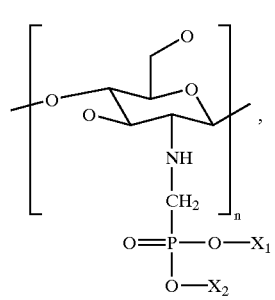

(2)

wherein
X$_1$ and X$_2$ are as defined for formula (1a) is used.

* * * * *